United States Patent [19]

Nunami et al.

[11] Patent Number: 5,312,826

[45] Date of Patent: May 17, 1994

[54] N,3-DISUBSTITUTED ALANINAMIDE DERIVATIVES

[75] Inventors: Ken-ichi Nunami, Kobe; Tameo Iwasaki, Nishinomiya; Kazuo Matsumoto, Ibaraki; Koji Yano, Hoya; Isao Yamaguchi, Tokyo, all of Japan

[73] Assignee: Tanabe Seiyaku Co., Ltd., Osaka, Japan

[21] Appl. No.: 901,234

[22] Filed: Jun. 19, 1992

[30] Foreign Application Priority Data

Jun. 21, 1991 [JP] Japan ................................. 3-247155

[51] Int. Cl.$^5$ ............... C07D 277/593; C07D 263/34;
C07D 233/66; C07C 69/612; A61K 31/235;
A61K 31/41
[52] U.S. Cl. ..................................... 514/371; 514/374;
514/397; 514/399; 514/533; 548/201; 548/233;
548/236; 548/237; 548/239; 548/334.5;
548/495; 560/37; 560/38; 560/40; 562/440;
562/443; 562/445
[58] Field of Search ............... 548/195, 201, 233, 237,
548/236, 239, 339; 514/371, 374, 397, 399, 533;
562/443, 448, 450; 560/37, 38, 40

[56] References Cited

U.S. PATENT DOCUMENTS

| | | | |
|---|---|---|---|
| 2,491,523 | 12/1947 | Sheehan et al. | 548/201 |
| 2,538,963 | 1/1951 | Dutcher et al. | 548/201 X |
| 3,804,820 | 4/1974 | Quitt et al. | 548/201 |
| 4,313,945 | 2/1982 | Wiederkehr et al. | 548/195 X |
| 4,331,806 | 5/1982 | Haugwitz | 548/201 X |
| 4,371,699 | 2/1983 | Ohashi et al. | 548/201 |
| 4,483,850 | 11/1984 | Patchett et al. | 424/177 |
| 4,513,009 | 4/1985 | Roques et al. | 514/513 |
| 4,524,212 | 6/1985 | Gordon et al. | 548/201 X |
| 4,602,002 | 7/1986 | Patchett et al. | 514/11 |
| 4,749,688 | 6/1988 | Haslanger et al. | 514/19 |

FOREIGN PATENT DOCUMENTS

| | | | |
|---|---|---|---|
| 0079464 | 5/1983 | European Pat. Off. | 548/201 |
| 0254032 | 1/1988 | European Pat. Off. | 514/19 |
| 0318377 | 5/1989 | European Pat. Off. | 514/11 |

Primary Examiner—Floyd D. Higel
Attorney, Agent, or Firm—Birch, Stewart, Kolasch & Birch

[57] ABSTRACT

Disclosed are a dicarboxylic acid compound represented by the formula (I):

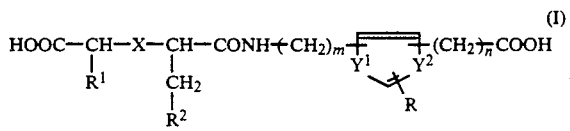

wherein R represents hydrogen atom, a lower alkyl group, phenyl group or hydroxyl group; $R^1$ represents a straight or branched alkyl group having 1 to 10 carbon atoms or a lower alkyl group substituted by a group selected from aryl group, a sulfur- or nitrogen-containing heterocyclic monocyclic group and a cycloalkyl group having 4 to 8 carbon atoms; $R^2$ represents a substituted or unsubstituted aryl group, a cycloalkyl group having 4 to 8 carbon atoms or a sulfur-containing or nitrogen-containing heterocylcic group; X represents sulfur atom, oxygen atom or a substituted or unsubstituted imino group; $Y^1$ represents imino group, oxygen atom or sulfur atom and $Y^2$ represents nitrogen atom, or $Y^1$ represents a vinylene group and $Y^2$ represents a group: —CH=; m represents 0 to 3; and n represents 0 or 1, an ester thereof or pharmaceutically acceptable salts thereof, and a process for preparing the same.

12 Claims, No Drawings

N,3-DISUBSTITUTED ALANINAMIDE DERIVATIVES

BACKGROUND OF THE INVENTION

This invention relates to a novel dicarboxylic acid derivative having antihypertensive activity and/or heart failure curing activity, and a process for preparing the same.

It has been known that atrial natriuretic peptide (ANP) secreted from atrial myocytes having strong diuretic, natriuretic and vasodilating activities and inhibiting activity on renin-angiotensin-aldosterone system is effective for curing hypertension and heart failure. However, ANP itself is a polypeptide and poorly absorbed in the digestive tracts, so that its administration route is limited to the parenteral route. On the other hand, it has been known that ANP is inactivated by neutral metalloendopeptidase, and the inhibitor of that enzyme increases the concentration of ANP in the blood and can also be used as a medicine for curing hypertension and/or heart failure.

SUMMARY OF THE INVENTION

An object of the present invention is to provide a novel dicarboxylic acid derivative having excellent metalloendopeptidase inhibiting activity that is useful as an antihypertensive drug and/or a medicine for curing heart failure.

The present invention is concerned with a dicarboxylic acid derivative represented by the formula (I):

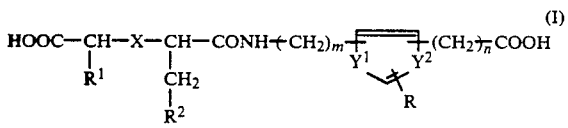

wherein R represents hydrogen atom, a lower alkyl group, phenyl group or hydroxyl group; $R^1$ represents a straight or branched alkyl group having 1 to 10 carbon atoms or a lower alkyl group substituted by a group selected from aryl group, a sulfur- or nitrogen-containing heterocyclic monocyclic group and a cycloalkyl group having 4 to 8 carbon atoms; $R^2$ represents a substituted or unsubstituted aryl group, a cycloalkyl group having 4 to 8 carbon atoms or a sulfur-containing or nitrogen-containing heterocylcic group; X represents sulfur atom, oxygen atom or a substituted or unsubstituted imino group; $Y^1$ represents imino group, oxygen atom or sulfur atom and $Y^2$ represents nitrogen atom, or $Y^1$ represents a vinylene group and $Y^2$ represents a group: —CH=; m represents 0 to 3; and n represents 0 or 1, an ester thereof or pharmaceutically acceptable salts thereof.

DESCRIPTION OF THE PREFERRED EMBODIMENTS

In the following, the present invention is explained in detail.

As a specific example of the desired compound of the present invention, there may be mentioned compounds in which $R^1$ is a straight or branched alkyl group having 1 to 10 carbon atoms, a lower alkyl group substituted by phenyl group, a lower alkyl group substituted by thienyl group or a lower alkyl group substituted by cyclohexyl group; $R^2$ is phenyl group, a phenyl group substituted by a lower alkoxy group, cyclohexyl group, thienyl group or indolyl group; and X is sulfur atom, oxygen atom, imino group or an imino group substituted by a lower alkyl group. Among them, a pharmaceutically preferred compound is a compound in which $R^1$ is a straight or branched alkyl group having 1 to 10 carbon atoms, a lower alkyl group substituted by phenyl group or a lower alkyl group substituted by thienyl group; $R^2$ is phenyl group, a phenyl group substituted by a lower alkoxy group or indolyl group; X is imino group or an imino group substituted by a lower alkyl group; $Y^1$ is imino group, oxygen atom or sulfur atom; $Y^2$ is nitrogen atom; m is 2; and n is 0, and a further preferred compound is a compound in which R is hydrogen atom, $R^1$ is a straight or branched alkyl group having 1 to 10 carbon atoms or a lower alkyl group substituted by phenyl group; $R^2$ is phenyl group or indolyl group; X is imino group; $Y^1$ is oxygen atom or sulfur atom; $Y^2$ is nitrogen atom; m is 2; and n is 0.

In the desired compound (I) of the present invention, a free carboxylic acid has excellent pharmacological activity, and an ester thereof is a prodrug which is metabolized in vivo and hydrolyzed to be a free carboxylic acid exhibiting activity. Thus, as such an ester residue, there may be used any one which does not participate in the production of pharmaceutical effects when hydrolyzed in vivo, and is pharmaceutically acceptable. As a specific example of the ester compound, there may be mentioned, for example, mono $C_{1-8}$ alkyl ester, di $C_{1-8}$ alkyl ester, mono(phenyl lower alkyl) ester, di(phenyl lower alkyl) ester and mono $C_{1-8}$ alkyl-mono(phenyl lower alkyl) ester. Among them, a preferred ester compound is a mono or di $C_{1-8}$ alkyl ester compound, and particularly preferred is a mono- or diethyl ester compound. Further, as a pharmaceutically acceptable salt of the desired compound (I) of the present invention or an ester thereof, there may be mentioned, for example, an inorganic acid addition salt such as hydrobromide, hydrochloride, sulfate, phosphate and nitrate; and an organic acid addition salt such as methanesulfonate, p-toluenesulfonate, oxalate, fumarate, maleate, tartrate and citrate.

The desired compound (I) of the present invention includes 4 kinds of optically active isomers based on two asymmetric carbon atoms and a mixture thereof. Among them, those in which both of two asymmetric carbon atoms have S configurations (hereinafter referred to "(S—S) isomer") are pharmaceutically particularly preferred.

In the desired compound (I) of the present invention, the lower alkyl group and the lower alkoxy group mean an alkyl group having 1 to 6 carbon atoms and an alkoxy group having 1 to 6 carbon atoms, respectively.

The desired compound (I), an ester thereof or a salt thereof can be administered orally or parenterally, and can be used as a pharmaceutical preparation by mixing with an excipient suitable for oral or parenteral administration. The pharmaceutical preparation may be either a solid preparation such as a tablet, a capsule and a powder or a liquid preparation such as a solution, a suspension and an emulsion Further, in the case of parenteral administration, it may also be used in a form suitable for injection.

The dose varies depending on an administration method, age, body weight and state of a patient and a kind of a disease to be cured, but, in general, it may be preferably about 1 to 100 mg/kg, particularly about 3 to 30 mg/kg per day.

According to the present invention, the desired compound (I) can be prepared by: (1) carrying out condensation reaction of a carboxylic acid compound represented by the formula (II):

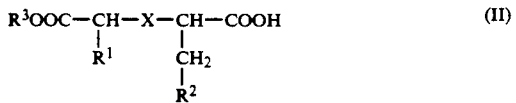

wherein $R^3$ represents a protective group for carboxyl group; $X^1$ represents sulfur atom, oxygen atom or a substituted or unsubstituted imino group; and $R^1$ and $R^2$ each have the same meanings as defined above, a salt thereof or a reactive derivative of its free carboxyl group, and an amine compound represented by the formula (III):

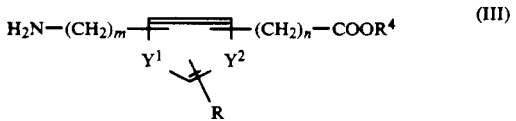

wherein $R^4$ represents a protective group for carboxy group; and R, $Y^1$, $Y^2$, m and n each have the same meanings as defined above, or a salt thereof, or (2) carrying out condensation reaction of an acetic acid compound represented by the formula (IV):

wherein $Z^1$ represents a reactive residue; and the other symbols each have the same meanings as defined above, and a compound represented by the formula (V):

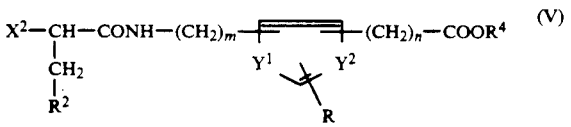

wherein $X^2$ represents thiol group, hydroxyl group or a substituted or unsubstituted amino group; and the other symbols each have the same meanings as defined above, or a salt thereof, then (3) carrying out lower alkylation of said product when $X^1$ is an unsubstituted imino group or $X^2$ is an unsubstituted amino group, if desired, and (4) removing the protective group(s) $R^3$ and/or $R^4$, if further desired.

As the protective groups $R^3$ and $R^4$ for carboxyl group, there may be mentioned a lower alkyl ester, a halogen-substituted lower alkyl ester, a phenyl-lower alkyl ester and a phenacyl ester. As the reactive residue $Z^1$, there may be suitably used a halogen atom, a lower alkylsulfonyloxy group and a lower alkylphenylsulfonyloxy group (e.g. p-toluenesulfonyloxy group).

As a salt of the carboxylic acid compound (II), an alkali metal salt and an alkaline earth metal salt may be suitably used, and as salts of the amine compound (III) and the compound (V), an inorganic salt such as a mineral acid salt and an organic acid salt may be suitably used.

The condensation reaction of the carboxylic acid compound (II) or a salt thereof and the amine compound (III) or a salt thereof may be carried out suitably in the presence of a dehydrating agent. As the dehydrating agent, any agent which can be used for synthesizing a peptide may be used, and there may be mentioned, for example, water-soluble carbodiimide such as 1-ethyl-3-(3-dimethylaminopropyl)carbodiimide, and dicyclohexylcarbodiimide.

On the other hand, the condensation reaction of the reactive derivative in carboxyl group of the carboxylic acid compound (II) and the amine compound (III) or a salt thereof, and the condensation reaction of the acetic acid compound (IV) and the compound (V) or a salt thereof may be carried out suitably in the presence or absence of an acid acceptor. As the acid acceptor, there may be used suitably any of an organic base such as tri-lower alkylamine, N,N- di-lower alkylamine and pyridine; and an inorganic base such as an alkali metal hydroxide an alkali metal hydrogen carbonate, an alkali metal carbonate and an alkali metal hydride. As the reactive derivative in carboxyl group of the carboxylic acid compound (II), there may be used those conventionally used in synthesizing a peptide, for example, any of an acid halide, an active ester, mixed acid anhydride and azide.

These reactions are preferably carried out in the presence or absence of a suitable solvent under cooling or at room temperature, particularly at $-30°$ C. to $30°$ C. The solvent is not particularly limited so long as it is inactive in the reactions, but may include, for example, dimethylformamide, tetrahydrofuran, dioxane, acetonitrile and hexamethylphosphoric triamide or a solvent mixture thereof.

In the starting compound (II) or (V), when $X^1$ is an unsubstituted imino group or $X^2$ is an unsubstituted amino group, the product obtained as described above may be further subjected to lower alkylation. The lower alkylation can be carried out according to a conventional method, for example, it can be carried out by reacting said product with a lower alkyl halide. The reaction with a lower alkyl halide can be carried out suitably in the presence of an acid acceptor in a solvent. As the lower alkyl halide, methyl iodide and ethyl iodide may be used suitably. As the acid acceptor and the solvent, there may be used the same ones described above. The reaction is preferably carried out under cooling or under heating, particularly at about room temperature.

The protective group(s) $R^3$ and/or $R^4$ can be removed from the product thus obtained by a conventional method such as catalytic hydrogenolysis and acidic hydrolysis depending on the kind of said protective group.

Among the above reactions, the reactions (1), (3) and (4) proceed without racemization, so that when an optically active starting compound is used, a corresponding optically active desired compound (I) can be obtained. Further, in the condensation reaction (2), nucleophilic substitution ($SN_2$ reaction) occurs on an asymmetric carbon atom. Since the reaction proceeds without racemization by selecting reaction conditions such as the kind of an acid acceptor suitably, an optically active desired compound having a desired configuration can be obtained by using an optically active starting compound previously having a suitable configuration. When the desired compound obtained is a racemic modification, it may be separated to the respective optically active isomers by a conventional method (e.g. chromatography).

The starting compounds (II) can be prepared by reacting the acetic acid compound (IV) with an acetic acid compound represented by the formula (VI):

$$X^2-CH-COOR^5 \\ | \\ CH_2 \\ | \\ R^2$$ (VI)

wherein $R^5$ represents a protective group for carboxyl group; and $R^2$ and $X^2$ each have the same meanings as defined above, in the presence of an acid acceptor (e.g. potassium carbonate) in a solvent (e.g. hexamethylphosphoric triamide), and then removing the protective group $R^5$.

The amine compound (III) in which R is hydrogen atom, $Y^1$ is oxygen atom, $Y^2$ is nitrogen atom and n is 0 can be prepared by carrying out cyclization reaction of an amino acid compound represented by the formula (VII):

$$R^6-NH-(CH_2)_m-COOH$$ (VII)

wherein $R^6$ represents a protective group for amino group; and m has the same meaning as defined above, and an isocyanoacetic acid compound represented by the formula (VIII):

$$CN-CH_2-COOR^4$$ (VIII)

wherein $R^4$ has the same meaning as defined above, in the presence of an acid acceptor (e.g. triethylamine) in a solvent (e.g. dimethylformamide), and then removing the protective group $R^6$. Further, the compound (III) in which n is 1 may be prepared by reacting the product obtained above with diazomethane and then treating the product with silver benzoate.

The amine compound (III) in which $Y^1$ is sulfur atom or nitrogen atom and $Y^2$ is nitrogen atom can be prepared by treating an oxazole ring of the amine compound (III) in which $Y^1$ is oxygen atom and $Y^2$ is nitrogen atom in a solvent (e.g. methanol) with an acid (e.g. hydrochloric acid) to effect single ring-opening and closing the ring again by a sulfurizing agent (e.g. a dimer of p-methoxyphenylthionophosphine sulfide) or an iminating agent (e.g. ammonium acetate). Further, the starting compound (III) having a substituent (R) on a ring can be obtained by selecting an acylating agent, a sulfurizing agent or an iminating agent suitably when recyclization reaction is carried out after opening the oxazole ring. Moreover, the compound (III) in which $Y^1$ is sulfur atom, $Y^2$ is nitrogen atom, m is 0 and n is 1 may be prepared according to the method described in Beil., 27, 336, and the compound (III) in which $Y^1$ is vinylene group and $Y^2$ is a group: —CH= may be prepared according to the method described in Beil., 14, 383.

The amine compound (V) can be prepared by carrying out condensation reaction of an acetic acid compound represented by the formula (IX):

$$X^3-CH-COOH \\ | \\ CH_2 \\ | \\ R^2$$ (IX)

wherein $X^3$ represents a protected substituted or unsubstituted amino group or a protected thiol group, or a reactive derivative of its carboxyl group and the amine compound (III) by, for example, the method described in the reaction of the compounds (II) and (III), and then removing the protective group at $X^3$.

Among the above reactions, the reactions of the acetic acid compound (IX) and the amine compound (III), and the acetic acid compound (IV) and the acetic acid compound (VI) can proceed without racemization as described in the above reaction (1) and reaction (2). Thus, by using an optically active compound as a starting material, an optically active compound (II) or (V) can be obtained. Further, when the compound obtained is a racemic modification, it may be separated to the respective optical isomers by a conventional method (e.g. chromatography).

EXAMPLES

The present invention is described in detail by referring to Examples.

EXAMPLE 1

(1) A mixture of 33 g of benzyl 2-bromo-4-phenylbutyrate, 22.1 g of (L)-phenylalanine tert-butyl ester, 13.8 g of potassium carbonate and 30 ml of hexamethylphosphoric triamide was stirred at room temperature overnight. Then, ethyl acetate was added to the mixture, and the insolubles were removed by filtration. The filtrate was washed and dried, and then the solvent was removed. The residue was purified by silica gel to obtain 16.6 g of N-((1S)-1-benzyloxycarbonyl-3-phenylpropyl)-(L)-phenylalanine tert-butyl ester and 9.9 g of N-((1R)-1-benzyloxycarbonyl-3-phenylpropyl)-(L)-phenylalanine tert-butyl ester as oily products, respectively.

(S—S) isomer

NMR CDCl$_3$) δ: 1.31 (s, 9H), 1.76~2.06 (m, 3H), 2.51~2.70 (m, 2H), 2.78~2.97 (m, 2H), 3.30~3.49 (m, 2H), 5.10 (s, 2H), 7.07~7.28 (m, 10H), 7.34 (s, 5H).

(2) After 4.73 g of the above (S-S) isomer and 30 ml of trifluoroacetic acid were stirred under ice cooling for 10 minutes and further at room temperature for 50 minutes, the solvent was removed. A 10 % potassium carbonate aqueous solution was added to the residue to effect neutralization, and the crystals formed were collected by filtration to obtain 3.09 g of N-((1S)-1-benzyloxycarbonyl-3-phenylpropyl)-(L)-phenylalanine.

M.P.: 141° to 143.5° C.

(3) A mixture of 4.2 g of the product obtained, 3.27 g of 4-benzyloxycarbonyl-5-(2-aminoethyl)oxazole.-monohydrobromide, 1.53 g of 1-hydroxybenzotriazole.-monohydrate, 1.4 ml of triethylamine, 1.9 g of 1-ethyl-3-(3-dimethylaminopropyl)carbodiimide.hydrochloride and 30 ml of dimethylformamide was stirred at −20° C. for 1 hour and then at room temperature overnight. The solvent was removed, and then ethyl acetate was added to the residue. The mixture was washed and dried, and then the solvent was removed. The residue was purified by silica gel column chromatography (solvent: chloroform-ethyl acetate) to obtain 4.52 g of 4-benzyloxycarbonyl-5-(2-[N-((1S)-1-benzyloxycarbonyl-3-phenylpropyl)-(L)-phenylalanyl]aminoethyl)oxazole as a colorless oily product.

NMR CDCl$_3$) δ: 1.68~1.97 (m, 2H), 2.38~2.76 (m, 3H), 2.97~3.59 (m, 7H), 4.95, 5.06 (ABq, 2H), 5.33 (s, 2H), 7.02–7.42 (m, 20H), 7.67 (s, 1H).

EXAMPLES 2 TO 4

(1) The corresponding starting compounds (IV) and (VI) were treated in the same manner as in Example 1-(1) to obtain compounds shown in the following Table 1.

TABLE 1

$$R^3OOC-\overset{*}{\underset{R^1}{CH}}-NH-\overset{*}{\underset{Bzl}{CH}}-COOC(CH_3)_3$$

| Example No. | $R^1$ | $R^3$ | Absolute configuration of asymmetric carbon atom substituted by $-R^1$ group | Physical properties |
|---|---|---|---|---|
| 2-(1) | $-CH_2CH_2C_6H_5$ | $C_2H_5$ | S | State: oily product |
|  |  |  | R | State: oily product |
| 3-(1) | $-(CH_2)_7-CH_3$ | Bzl | S | State: oily product |
|  |  |  | R | State: oily product |
| 4-(1) | $-(CH_2)_7-CH_3$ | $C_2H_5$ | S | State: oily product |
|  |  |  | R | State: oily product |

Note 1: Bzl represents benzyl group (hereinafter the same).
Note 2: *represents an asymmetric carbon atom having an S configuration (hereinafter the same).

(2) The products having (S—S) configurations obtained in the above (1) were treated in the same manner as in Example 1-(2) to obtain (S—S) isomer compounds shown in the following Table 2.

TABLE 2

$$R^3OOC-\overset{*}{\underset{R^1}{CH}}-NH-\overset{*}{\underset{Bzl}{CH}}-COOH$$

| Example No. | $R^1$ | $R^3$ | Physical properties |
|---|---|---|---|
| 2-(2) | $-CH_2CH_2C_6H_5$ | $C_2H_5$ | M.P.: 134 to 137° C. |
| 3-(2) | $-(CH_2)_7-CH_3$ | Bzl | M.P.: 129 to 131° C. |
| 4-(2) | $-(CH_2)_7-CH_3$ | $C_2H_5$ | M.P.: 110 to 114° C. |

(3) The products obtained in the above (2) were treated in the same manner as in Example 1-(3) to obtain (S—S) isomer compounds shown in the following Table 3.

TABLE 3

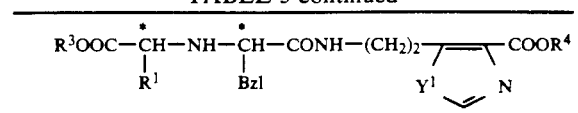

| Example No. | $R^1$ | $R^3$ | $Y^1$ | $R^4$ | Physical properties |
|---|---|---|---|---|---|
| 2-(3) | $-CH_2CH_2C_6H_5$ | $C_2H_5$ | S | $C_2H_5$ | State: syrup NMR (CDCl$_3$) δ: 1.18 (t, 3H) 1.41 (t, 3H) 1.71~1.88 (m, 2H) 2.49~2.80 (m, 3H) 3.05~3.63 (m, 5H) 3.93~4.12 (m, 2H) |

TABLE 3-continued

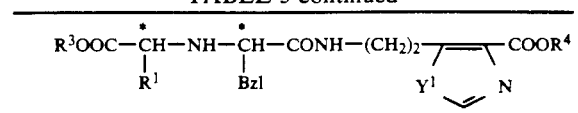

| Example No. | $R^1$ | $R^3$ | $Y^1$ | $R^4$ | Physical properties |
|---|---|---|---|---|---|
|  |  |  |  |  | 4.40 (q, 2H) 7.10~7.36 (m, 10H) 8.60 (s, 1H) |
| 3-(3) | $-(CH_2)_7-CH_3$ | Bzl | O | $C_2H_5$ | State: syrup NMR (CDCl$_3$) δ: 0.78 (t, 3H) 1.16 (t, 3H) 1.15~1.60 (m, 12H) 1.40~1.54 (m, 2H) 2.65~2.74 (m, 1H) 2.98~3.17 (m, 2H) 3.19~3.32 (m, 2H) 3.54~3.68 (m, 2H) 3.93~4.08 (m, 1H) 5.00 (q, 2H) 7.10~7.39 (m, 10H) 7.76 (s, 1H) |
| 4-(3) | $-(CH_2)_7-CH_3$ | $C_2H_5$ | O | Bzl | M.P. 58~59° C. |

EXAMPLES 5 TO 14

The corresponding starting compounds (II) and (III) were treated in the same manner as in Example 1-(3) to obtain the desired compounds of (S-S) isomers shown in the following Tables 4 to 6.

TABLE 4

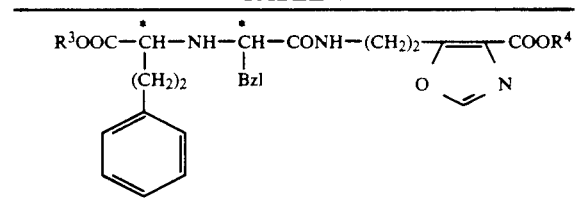

| Example No. | $R^3$ | $R^4$ | Physical properties |
|---|---|---|---|
| 5 | Bzl | $C_2H_5$ | State: syrup NMR (CDCl$_3$) δ: 1.36 (t, 3H) 1.64 (br-s, 1H) 1.76~1.96 (m, 2H) 2.42~2.78 (m, 3H) 2.88~3.32 (m, 5H) 3.41~3.64 (m, 2H) 4.34 (q, 2H) 5.00 (q, 2H) 7.04~7.37 (m, 15H) 7.67 (s, 1H) |
| 6 | $C_2H_5$ | Bzl | State: syrup NMR (CDCl$_3$) δ: 1.17 (t, 3H) 1.69 (br-s, 1H) 1.68~1.95 (m, 2H) 2.46~2.76 (m, 3H) 3.03~3.30 (m, 5H) 3.39~3.60 (m, 2H) 4.02 (q, 2H) 5.34 (s, 2H) 7.10~7.43 (m, 15H) 7.70 (s, 1H) |
| 7 | $C_2H_5$ | $C_2H_5$ | State: syrup NMR (CDCl$_3$) δ: 1.17 (t, 3H) 1.38 (t, 3H) 1.70 (br-s, 1H) 1.76~1.96 (m, 2H) 2.47~2.78 (m, 3H) 2.95~3.30 (m, 5H) 3.43~3.63 (m, 2H) 3.90~4.11 (m, 2H) 4.37 (q, 2H) |

TABLE 4-continued

R³OOC—CH—NH—CH—CONH—(CH₂)₂—[oxazole]—COOR⁴
      |      |
      (CH₂)₂  Bzl
      |
      C₆H₅

| Example No. | R³ | R⁴ | Physical properties |
|---|---|---|---|
| | | | 7.12~7.36 (m, 10H) |
| | | | 7.71 (s, 1H) |

TABLE 5

R³OOC—CH—NH—CH—CONH—(CH₂)₂—[oxazole]—COOR⁴
      |      |
      R¹    Bzl

| Example No. | R¹ | R³ | R⁴ | Physical properties |
|---|---|---|---|---|
| 8 | —CH₂CH₂C₆H₅ | Bzl | CH₃ | State: syrup<br>NMR (CDCl₃) δ:<br>1.7~2.05 (m, 3H)<br>2.42~2.69 (m, 2H)<br>2.84 (dd, 1H)<br>3.07 (dd, 1H)<br>3.19 (t, 1H)<br>3.36 (dd, 1H)<br>3.85 (s, 3H)<br>4.75 (d, 2H)<br>4.97, 5.07 (ABq, 2H)<br>7.03~7.38 (m, 15H)<br>7.66 (t, 1H)<br>7.72 (s, 1H) |
| 9 | —CH₂CH₂C₆H₅ | Bzl | C(CH₃)₃ | State: syrup<br>NMR (CDCl₃) δ:<br>1.58 (s, 9H)<br>1.73~1.95 (m, 2H)<br>2.42~2.63 (m, 2H)<br>2.66~2.79 (m, 1H)<br>3.02~3.21 (m, 2H)<br>3.25~3.36 (m, 1H)<br>3.39~3.62 (m, 2H)<br>5.00 (q, 2H)<br>7.03~7.37 (m, 15H)<br>7.64 (s, 1H) |
| 10 | —(CH₂)₇—CH₃ | C₂H₅ | C₂H₅ | State: syrup<br>NMR (CDCl₃) δ:<br>0.87 (t, 3H)<br>1.16 (t, 3H)<br>1.20~1.32 (m, 12H)<br>1.41 (t, 3H)<br>1.38~1.55 (m, 2H)<br>2.68~2.79 (m, 1H)<br>2.97~3.16 (m, 3H)<br>3.22~3.40 (m, 2H)<br>3.56~3.72 (m, 2H)<br>4.01 (q, 2H)<br>4.39 (q, 2H)<br>7.16~7.35 (m, 5H)<br>7.78 (s, 1H) |

TABLE 6

R³OOC—CH—NH—CH—CONH—(CH₂)₂—[Y¹/N ring]—COOR⁴
      |      |
      R¹    Bzl

| Example No. | R¹ | R³ | Y¹ | R⁴ | Physical properties |
|---|---|---|---|---|---|
| 11 | —CH₂CH₂C₆H₅ | Bzl | S | C₂H₅ | State: syrup<br>NMR (CDCl₃) δ: |

TABLE 6-continued

R³OOC—CH—NH—CH—CONH—(CH₂)₂—[Y¹/N ring]—COOR⁴
      |      |
      R¹    Bzl

| Example No. | R¹ | R³ | Y¹ | R⁴ | Physical properties |
|---|---|---|---|---|---|
| | | | | | 1.40 (t, 3H)<br>1.72~1.98 (m, 2H)<br>2.41~2.63 (m, 2H)<br>2.68~2.80 (m, 1H)<br>3.00~3.23 (m, 2H)<br>3.22~3.33 (m, 1H)<br>3.41~3.60 (m, 2H)<br>4.39 (q, 2H)<br>4.92~5.10 (m, 2H)<br>7.03~7.67 (m, 15H)<br>8.56 (s, 1H) |
| 12 | —CH₂CH₂C₆H₅ | C₂H₅ | S | Bzl | State: syrup<br>NMR (CDCl₃) δ:<br>1.78 (t, 3H)<br>1.73~1.95 (m, 2H)<br>2.52~2.78 (m, 3H)<br>3.03~3.62 (m, 7H)<br>3.94~4.12 (m, 2H)<br>5.38 (s, 2H)<br>7.09~7.70 (m, 15H)<br>8.56 (s, 1H) |
| 13 | —(CH₂)₇—CH₃ | Bzl | O | Bzl | M.P. 58~59° C. |
| 14 | —CH₂CH₂C₆H₅ | Bzl | S | Bzl | State: syrup<br>NMR (CDCl₃) δ:<br>1.72~1.98 (m, 2H)<br>2.39~2.62 (m, 2H)<br>2.64~2.78 (m, 1H)<br>2.97~3.20 (m, 2H)<br>3.24~3.33 (m, 1H)<br>3.34~3.57 (m, 4H)<br>4.90~5.09 (m, 2H)<br>5.37 (s, 2H)<br>7.01~7.48 (m, 20H)<br>8.55 (s, 1H) |

EXAMPLE 15

1.8 g of 4-benzyloxycarbonyl-5-{2-[N-((1S)-1-benzyloxycarbonyl-3-phenylpropyl)-(L)-phenylalanyl]aminoethyl}oxazole was subjected to catalytic hydrogenolysis in 50 ml of dimethylformamide in the presence of 100 mg of palladium-black at 3 atmospheric pressure for 5 hours. After removal of the catalyst by filtration, the solvent was removed. The crystals obtained were recrystallized from methanol to obtain 1.1 g of 4-carboxy-5-{2-[N-((1S)-1-carboxy-3-phenylpropyl)-(L)-phenylalanyl]aminoethyl}oxazole.

M.P.: 179° to 181° C. (decomposed)

EXAMPLES 16 TO 22

The products obtained in Examples 3 to 6, 8, 9 and 13 were treated in the same manner as in Example 15 to obtain the desired products of (S—S) isomers shown in the following Tables 7 and 8.

TABLE 7

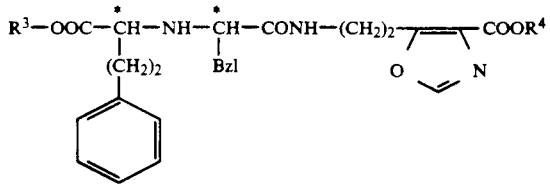

| Example No. | R³ | R⁴ | Physical properties |
|---|---|---|---|
| 16 | $C_2H_5$ | H | M.P.: 127~129° C. |
|  |  |  | Hydrochloride: 170~171° C. |
| 17 | H | $C_2H_5$ | M.P.: 225~227° C. (dec.) |
| 18 | H | $CH_3$ | M.P.: 221° C. (dec.) |
| 19 | H | $C(CH_3)_3$ | M.P.: 204° C. (dec.) |

TABLE 8

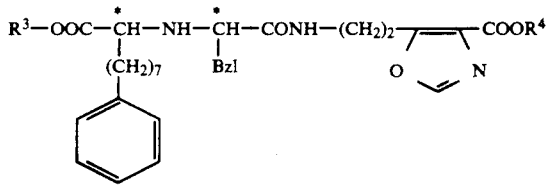

| Example No. | R³ | R⁴ | Physical properties |
|---|---|---|---|
| 20 | H | H | M.P.: 170~174° C. |
| 21 | $C_2H_5$ | H | M.P.: 126~128° C. |
| 22 | H | $C_2H_5$ | M.P.: 165~169° C. |

EXAMPLE 23

A mixture of 2.2 g of 4-benzyloxycarbonyl-5-{2-[N-((1S)-1-ethoxycarbonyl-3-phenylpropyl)-(L)-phenylalanyl]aminoethyl}thiazole and 30 ml of a 25% hydrogen bromide-acetic acid solution was stirred at room temperature for one day. After removing the solvent, the mixture was neutralized with a 10% potassium carbonate aqueous solution. The crystals obtained were recrystallized from a methanol-isopropyl ether mixed solution to obtain 1.27 g of 4-carboxy-5-{2-[N-((1S)-1-ethoxycarbonyl-3-phenylpropyl)-(L)-phenylalanyl]aminoethyl}thiazole.

M.P.: 121° to 124° C.

EXAMPLES 24 AND 25

The products obtained in Examples 11 and 14 were treated in the same manner as in Example 23 to obtain the desired compounds of (S—S) isomers shown in the following Table 9.

TABLE 9

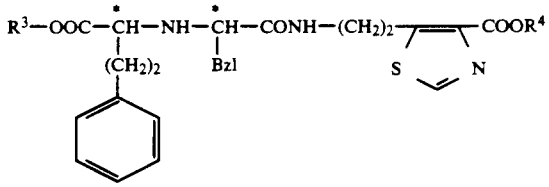

| Example No. | R³ | R⁴ | Physical properties |
|---|---|---|---|
| 24 | H | $C_2H_5$ | M.P.: 211~212° C. |
| 25 | H | H | M.P.: 174° C. (dec.) |

EXAMPLES 26 TO 35

(1) A mixture of 5.91 g of ethyl (2R)-3-phenyl-2-*p*-toluenesulfonyloxy propionate, 15.7 g of (L)-phenylalanine benzyl ester, 2.91 g of di(isopropyl)ethylamine and 5 ml of hexamethylphosphoric triamide was stirred at 70° C. for 2 days, and then ethyl acetate was added thereto. The mixture was washed and dried, and then the solvent was removed. The residue was purified by silica gel column chromatography (solvent: hexane:ethyl acetate=9:1) to obtain 4.45 g (Yield: 69%) of N-((1S)-1-ethoxycarbonyl-2-phenylethyl)-(L)-phenylalanine benzyl ester as an oily product.

NMR (in $CDCl_3$) δ: 1.08 (t, 3H), 2.95 (t, 4H), 3.55~3.69 (m, 2H), 3.99 (q, 2H), 5.01 (ABq, 2H), 7.08~7.33 (m, 15H).

The corresponding starting compounds were treated in the same manner as described above to obtain compounds shown in the following Table 10.

TABLE 10

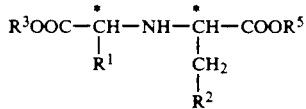

| Example No. | R¹ | R² | R³ | R⁵ | Physical properties |
|---|---|---|---|---|---|
| 27-(1) | —$CH_2CH_2$—⟨H cyclohexyl⟩ | ⟨phenyl⟩ | Bzl | —$C(CH_3)_3$ | State: oily product |
| 28-(1) | —$CH_2CH(CH_3)_2$ | " | " | " | " |
| 29-(1) | —$CH_2CH_2$—⟨phenyl⟩ | ⟨H cyclohexyl⟩ | " | " | " |
| 30-(1) | —$(CH_2)_7CH_3$ | ⟨phenyl⟩ | —$C(CH_3)_3$ | Bzl | " |

TABLE 10-continued $$R^3OOC-\overset{*}{C}H-NH-\overset{*}{C}H-COOR^5$$
$$\phantom{R^3OOC-}\underset{R^1}{|}\phantom{-NH-}\underset{\underset{R^2}{|}}{\underset{CH_2}{|}}$$

| Example No. | $R^1$ | $R^2$ | $R^3$ | $R^5$ | Physical properties |
|---|---|---|---|---|---|
| 31-(1) | $-CH_2CH_2-\phenyl$ | " | " | " | " |
| 32-(1) | Isopentyl | " | Bzl | $-C(CH_3)_3$ | " |
| 33-(1) | $-CH_2CH_2-\phenyl$ | $-\phenyl-OCH_3$ (p) | $-CH_2CH_3$ | Bzl | " |
| 34-(1) | $-CH_2-\phenyl$ | indol-3-yl | $-CH_3$ | " | M.P. = 87~89° C. |
| 35-(1) | " | $-\phenyl-OCH_3$ (p) | " | " | State: oily product |

(2) The products obtained above were treated in the same manner as in Example 1-(2) or Example 15 to obtain compounds shown in the following Table 11.

TABLE 11

$$R^3OOC-\overset{*}{C}H-NH-\overset{*}{C}H-COOH$$
$$\phantom{R^3OOC-}\underset{R^1}{|}\phantom{-NH-}\underset{\underset{R^2}{|}}{\underset{CH_2}{|}}$$

| Example No. | $R^1$ | $R^2$ | $R^3$ | Physical properties |
|---|---|---|---|---|
| 26-(2) | $-CH_2-\phenyl$ | phenyl | $-CH_2CH_3$ | M.P. = 150~151° C. |
| 27-(2) | $-CH_2CH_2-\cyclohexyl$ | " | Bzl | M.P. = 121~123° C. |
| 28-(2) | $-CH_2CH(CH_3)_2$ | " | " | M.P. = 146~148° C. |
| 29-(2) | $-CH_2CH_2-\phenyl$ | cyclohexyl | " | M.P. = 126~129° C. |
| 30-(2) | $-(CH_2)_7CH_3$ | phenyl | $-C(CH_3)_3$ | M.P. = 150~152° C. |
| 31-(2) | $-CH_2CH_2-\phenyl$ | " | " | M.P. = 144~146° C. |
| 32-(2) | Isopentyl | " | Bzl | M.P. = 146~148° C. |

TABLE 11-continued $$R^3OOC-\overset{*}{C}H-NH-\overset{*}{C}H-COOH$$
$$\underset{R^1}{|} \quad \underset{\underset{R^2}{|}}{CH_2}$$

| Example No. | R¹ | R² | R³ | Physical properties |
|---|---|---|---|---|
| 33-(2) | $-CH_2CH_2-\phenyl$ | $-\phenyl-OCH_3$ (para) | $-CH_2CH_3$ | Oily product |
| 34-(2) | $-CH_2-\phenyl$ | indol-3-ylmethyl (3-indolyl) | $-CH_3$ | M.P. = 110~112° C. |
| 35-(2) | " | $-\phenyl-OCH_3$ (para) | " | Oily product |

(3) The products obtained above were treated in the same manner as in Example 1-(3) to obtain compounds shown in the following Tables 12 and 13.

TABLE 12

$$R^3OOC-\overset{*}{C}H-NH-\overset{*}{C}H-CONH-(CH_2)_2-\underset{O\diagdown N}{\text{(oxazole)}}-COOBzl$$
$$\underset{R^1}{|} \quad \underset{\underset{R^2}{|}}{CH_2}$$

| Example No. | R¹ | R² | R³ | Physical properties |
|---|---|---|---|---|
| 26-(3) | $-CH_2-\phenyl$ | $-\phenyl$ | $-CH_2CH_3$ | State: Syrup<br>NMR (in CDCl₃) δ: 1.13 (t, 3H), 1.71 (s, 1H), 2.45~2.62 (m, 2H), 2.74~3.38 (m, 8H), 3.89~4.17 (m, 2H), 5.39 (s, 2H), 6.36 (m, 1H), 7.11~7.49 (m, 15H), 7.75 (s, 1H) |
| 27-(3) | $-CH_2CH_2-$cyclohexyl (H) | " | Bzl | State: Syrup<br>NMR (in CDCl₃) δ: 0.65~1.83 (m, 15H), 2.67~2.81 (m, 1H), 2.98~3.18 (m, 2H), 3.18~3.41 (m, 3H), 3.52~3.71 (m, 2H), 4.91~5.34 (m, 4H), 7.10~7.42 (m, 15H), 7.74 (s, 1H) |
| 28-(3) | $-CH_2CH(CH_2)_3$ | " | " | M.P. 93~95° C. |
| 29-(3) | $-CH_2CH_2-\phenyl$ | cyclohexyl (H) | " | State: Syrup<br>NMR (in CDCl₃) δ: 0.72~1.04 (m, 2H), 1.06~1.78 (m, 11H), 1.78~2.05 (m, 3H), 2.47~2.79 (m, 2H), 3.12~3.30 (m, 2H), 3.30~3.72 (m, 2H), 5.13 (s, 2H), 5.32 (s, 2H), 7.07~7.46 (m, 15H), 7.69 (s, 1H) |
| 30-(3) | $-(CH_2)_7CH_3$ | $-\phenyl$ | $-C(CH_3)_3$ | State: Syrup<br>NMR (in CDCl₃) δ: 0.83~0.86 (m, 3H), 1.11~1.58 (m, 14H), 1.36 (s, 9H), 2.70~3.18 (m, 3H), 3.18~3.39 (m, 3H), 3.42~3.70 (m, 2H), 5.37 (s, 2H), 7.13~7.43 (m, 10H), 7.76 (s, 1H) |

TABLE 12-continued $$R^3OOC-\overset{*}{C}H-NH-\overset{*}{C}H-CONH-(CH_2)_2-\underset{O\diagdown N}{\diagup\!\!=\!\!\diagdown}-COOBzl$$
$$\qquad\qquad\;\;|\qquad\qquad\;\;|$$
$$\qquad\qquad\;\;R^1\qquad\qquad CH_2$$
$$\qquad\qquad\qquad\qquad\qquad\;\;|$$
$$\qquad\qquad\qquad\qquad\qquad R^2$$

| Example No. | R¹ | R² | R³ | Physical properties |
|---|---|---|---|---|
| 31-(3) | —CH₂CH₂—C₆H₅ | " | " | State: Syrup<br>NMR (in CDCl₃) δ: 1.39 (s, 9H), 1.66~1.92 (m, 2H), 1.93 (broad s, 1H), 2.46~2.84 (m, 3H), 2.95~3.28 (m, 7H), 5.34 (s, 2H), 7.11~7.43 (m, 16H), 7.68 (s, 1H) |
| 32-(3) | Isopentyl | " | Bzl | M.P. 67~69° C. |

TABLE 13

$$R^3OOC-\overset{*}{C}H-NH-\overset{*}{C}H-CONH-(CH_2)_2-\underset{Y^1\diagdown N}{\diagup\!\!=\!\!\diagdown}-COOR^4$$
$$\qquad\qquad\;\;|\qquad\qquad\;\;|$$
$$\qquad\qquad\;\;R^1\qquad\qquad CH_2$$
$$\qquad\qquad\qquad\qquad\qquad\;\;|$$
$$\qquad\qquad\qquad\qquad\qquad R^2$$

| Example No. | R¹ | R² | R³ | R⁴ | Y¹ | Physical properties |
|---|---|---|---|---|---|---|
| 33-(3) | —CH₂CH₂—C₆H₅ | —C₆H₄—OCH₃ | —CH₂CH₃ | —CH₂CH₃ | O | State: Syrup<br>NMR (in CDCl₃) δ: 1.19 (t, 3H), 1.38 (t, 3H), 1.80~1.97 (m, 3H), 2.47~2.74 (m, 3H), 2.88~3.27 (m, 6H), 3.43~3.63 (m, 2H), 3.79 (s, 3H), 3.93~4.17 (m, 2H), 4.36 (q, 2H), 6.72, 6.94 (ABq, 2H), 7.07~7.31 (m, 7H), 7.71 (s, 1H) |
| 34-(3) | —CH₂—C₆H₅ | indol-3-yl-CH₂ (3-indolylmethyl) | —CH₃ | Bzl | " | State: Syrup<br>NMR (in CDCl₃) δ: 1.97 (broad s, 1H), 2.40~2.52 (m, 1H), 2.71~2.95 (m, 5H), 3.16~3.21 (m, 2H), 3.25 (s, 3H), 3.28~3.40 (m, 2H), 5.37 (s, 2H), 6.39~6.44 (m, 1H), 7.02~7.66 (m, 15H), 7.71 (s, 1H), 8.18 (broad s, 1H) |
| 35-(3) | " | —C₆H₄—OCH₃ | " | —CH₂CH₃ | " | State: Syrup<br>NMR (in CDCl₃) δ: 1.42 (t, 3H), 1.77 (broad s, 1H), 2.46~2.59 (m, 2H), 2.76~3.06 (m, 6H), 3.16~3.42 (m, 2H), 3.54 (s, 3H), 3.80 (s, 3H), 4.39 (q, 2H), 6.38 (broad s, 1H0, 6.85, 7.07 (ABq, 2H), 7.15~7.34 (m, 5H), 7.76 (s, 1H) |

EXAMPLES 36 TO 37

The corresponding starting compounds were treated in the same manner as in Example 1-(3) to obtain compounds shown in the following Tables 14 and 15.

TABLE 14

$$Bzl-OOC-\overset{*}{C}H-NH-\overset{*}{C}H-CONH-(CH_2)_2-\underset{O\diagdown N}{\diagup\!\!=\!\!\diagdown}-COOR^4$$
$$\qquad\qquad\;\;|\qquad\qquad\;\;|\qquad\qquad\qquad\qquad\qquad\;\;|$$
$$\qquad\qquad(CH_2)_2\qquad Bzl\qquad\qquad\qquad\qquad\qquad R$$
$$\qquad\qquad\;\;|$$
$$\qquad\qquad C_6H_5$$

| Example No. | R⁴ | R | Physical properties |
|---|---|---|---|
| 36 | Bzl | —CH₃ | State: Syrup<br>NMR (in CDCl₃) δ: 1.62~1.95 (m, 2H), 2.45~3.60 (m, 10H), 2.38 (s, 3H), 4.94, 5.05 (ABq, 2H), 5.31 (s, 2H), 7.02~7.39 |

TABLE 14-continued

Bzl—OOC—*CH—NH—*CH—CONH—(CH₂)₂—⟨O,N ring with R⟩—COOR⁴
        |              |
       (CH₂)₂          Bzl
        |
       Ph

| Example No. | R⁴ | R | Physical properties |
|---|---|---|---|
| 37 | " | Ph | (m, 20H)<br>State: Syrup<br>NMR (in CDCl₃) δ: 1.67~1.83 (m, 2H), 1.90 (broad s, 1H), 2.32~2.61 (m, 2H), 2.68~2.79 (m, 1H), 3.00~3.69 (m, 8H), 4.94, 5.04 (ABq, 2H), 5.37 (s, 2H), 6.93~7.55 (m, 24H), 8.00~8.05 (m, 2H) |
| 38 | n-Oct | H | State: Syrup<br>NMR (in CDCl₃) δ: 0.03~0.90 (m, 3H), 1.18~1.46 (m, 10H), 1.63~2.00 (m, 4H), 2.41~2.65 (m, 8H), 2.67~2.80 (m, 1H), 3.01~3.15 (m, 1H), 3.16~3.36 (m, 4H), 3.37~3.67 (m, 2H), 4.24~4.31 (m, 2H), 4.91~5.10 (m, 2H), 7.03~7.37 (m, 15H), 7.67 (s, 1H) |
| 39 | n-Bu | " | State: Syrup<br>NMR (in CDCl₃) δ: 0.89~0.97 (m, 2H), 1.32~1.51 (m, 2H), 1.64~2.00 (m, 4H), 2.41~2.65 (m, 2H), 2.67~2.80 (m, 1H), 3.01~3.15 (m, 1H), 3.16~3.36 (m, 4H), 3.37~3.67 (m, 2H), 4.24~4.31 (m, 2H), 4.91~5.10 (m, 2H), 7.03~7.37 (m, 15H), 7.67 (s, 1H) |
| 40 | i-Bu | " | State: Syrup<br>NMR (in CDCl₃) δ: 1.72~1.96 (m, 2H), 2.41~2.62 (m, 2H), 2.64~2.79 (m, 1H), 3.01~3.11 (m, 1H), 3.12~3.32 (m, 4H), 3.38~3.63 (m, 2H), 4.01~4.10 (m, 2H), 4.92~5.10 (m, 2H), 7.03~7.39 (m, 15H), 7.67 (s, 1H) |
| 41 | i-Pr | " | State: Syrup<br>NMR (in CDCl₃) δ: 1.82~2.05 (m, 2H), 2.51~2.59 (m, 2H), 2.80~3.00 (m, 1H), 3.08~3.11 (m, 1H), 3.12~3.25 (m, 2H), 3.26~3.55 (m, 4H), 4.97~5.11 (m, 2H), 5.15~5.29 (m, 1H), 7.03~7.38 (m, 15H), 7.66 (s, 1H) |
| 42 | Bzl | —OH | State: Syrup<br>NMR (in CDCl₃) δ: 1.70~1.91 (m, 2H), 2.40~2.61 (m, 2H), 2.68~2.80 (m, 1H), 2.82~2.95 (m, 2H), 2.98~3.10 (m, 1H), 3.12~3.24 (m, 1H), 3.36~3.45 (m, 1H), 3.39~3.52 (m, 2H), 4.90~5.10 (m, 2H), 5.24 (s, 2H), 7.01~7.37 (m, 20H), 8.38 (broad s, 1H) |

TABLE 15

R³OOC—*CH—NH—*CH—CONH—(CH₂)ₘ—⟨Y¹,N ring⟩—COOR⁴
        |        |
        R¹      Bzl

| Example No. | R¹ | R³ | R⁴ | Y¹ | m | Physical properties |
|---|---|---|---|---|---|---|
| 43 | —CH₂CH₂—Ph | t-Bu | Bzl | S | 2 | State: Syrup<br>NMR (in CDCl₃) δ: 1.39 (s, 9H), 1.63~1.92 (m, 2H), 2.43~2.70 (m, 2H), 2.78 (dd, 1H), 2.93~3.10 (m, 2H), 3.22~3.56 (m, 5H), 5.38 (s, 2H), 7.10~7.48 (m, 16H), 8.58 (s, 1H) |
| 44 | —CH₂—Ph | Et | Et | " | " | State: Syrup<br>NMR (in CDCl₃) δ: 1.14 (t, 3H), 1.47 (t, 3H), 1.50 (broad s, 1H), 2.40~3.41 (m, 10H), 3.89~4.09 (m, 2H), 4.46 (q, 2H), 6.43 (broad s, 1H), 7.11~7.38 (m, 10H), 8.64 (s, 1H) |
| 45 | —CH₂CH₂—Ph | CH₃ | CH₃ | O | 1 | State: Syrup<br>NMR (in CDCl₃) δ: 1.5~2.0 (m, 4H), 2.5~2.9 (m, 2H), 3.07~3.47 (m, 2H), 3.42 (d, 2H), 3.75 (s, 3H), 3.93 (s, 3H), 6.93~7.31 (m, 1H), 7.75 (s, 1H) |

TABLE 15-continued $$R^3OOC-\overset{*}{\underset{R^1}{CH}}-NH-\overset{*}{\underset{Bzl}{CH}}-CONH-(CH_2)_m-\underset{Y^1\diagdown N}{\diagup=\diagdown}-COOR^4$$

| Example No. | $R^1$ | $R^3$ | $R^4$ | $Y^1$ | m | Physical properties |
|---|---|---|---|---|---|---|
| 46 | " | Bzl | Bzl | " | 3 | State: Syrup<br>NMR (in CDCl₃) δ: 1.63 (s, 1H), 1.72~1.96 (m, 4H), 2.52~2.70 (m, 2H), 2.75~3.34 (m, 8H), 4.97, 5.07 (ABq, 2H), 5.3 (s, 2H), 7.01~7.39 (m, 20H), 7.73 (s, 1H) |
| 47 | " | " | " | NH | 2 | State: Syrup<br>NMR (in CDCl₃) δ: 1.6~2.2 (m, 2H), 2.4~3.7 (m, 8H), 4.96, 5.06 (ABq, 2H), 5.32 (s, 2H), 7.00~8.44 (m, 21H) |

EXAMPLE 48

(1) A mixture of 2.56 g of (2S)-3-(2-thienyl)-2-(benzyloxycarbonylamino)propionic acid, 2.39 g of 4-benzyloxycarbonyl-5-(2-aminoethyl)oxazole.hydrobromide, 1.42 g of 1-hydroxybenzotriazole hydrate and 30 ml of dimethylformamide was cooled to −20° C., and 1.77 g of 1-ethyl-3-(3-dimethylaminopropyl)carbodiimide.hydrochloride was added thereto. After 10 minutes, 0.93 g of triethylamine was added to the mixture, and the temperature of the mixture was gradually returned to room temperature and the mixture was stirred overnight. The solvent was removed, and ethyl acetate was added to the residue. The mixture was washed and dried, and then the solvent was removed. The residue was purified by silica gel column chromatography (solvent: chloroform:ethyl acetate=19:1) to obtain 3.5 g of 4-benzyloxycarbonyl-5-{2-[N-((2S)-3-(2-thienyl)-2-(benzyloxycarbonylamino)propionyl)amino]ethyl}oxazole as syrup.

NMR (in CDCl₃) δ: 3.15~3.28 (m, 4H), 3.46~3.59 (m, 2H), 4.35 (m, 1H), 5.09 (s, 2H), 5.31 (s, 3H), 6.47 (br s, 1H), 6.75 (m, 1H), 6.83~6.88 (m, 1H), 7.09~7.12 (m, 1H), 7.32~7.42 (m, 10H), 7.69 (s, 1H).

(2) A mixture of 2.67 g of the product obtained and 20 ml of a 25% hydrogen bromide-acetic acid solution was stirred at room temperature for 10 minutes. Then, the solvent was removed, and the residue was powdered by adding ethyl ether. A mixture of 1.67 g of the powder obtained, 1.67 g of (1R)-1-benzyloxycarbonyl-1-(p-toluenesulfonyloxy)-3-phenylpropane, 1.75 ml of triethylamine and 20 ml of hexamethylphosphoric triamide was stirred at 75° C. overnight, and then ethyl acetate was added thereto. The mixture was washed and dried, and then the solvent was removed. The residue was purified by silica gel column chromatography (solvent: chloroform:ethyl acetate =98:2) to obtain 2.1 g of 4-benzyloxycarbonyl-5-{2-[N-((2S)-3-(2-thienyl)-2-(N-((1S)-1-benzyloxycarbonyl-3-phenylpropyl)amino)propionyl)amino]ethyl}oxazole.

M.P.: 81°~83° C.

EXAMPLES 49 TO 51

(1) The corresponding starting compounds were treated in the same manner as in Example 48-(1) to obtain the following compounds.

49-(1): 4-benzyloxycarbonyl-5-{2-(N-benzyloxycarbonyl-(L)-phenylalanyl)aminoethyl}oxazole
M.P.: 148°~149° C.

50-(1): 3-benzyloxycarbonyl-1-(N-benzyloxycarbonyl-(L)-phenylalanyl)amino}benzene
M.P.: 141°~143° C.

51-(1): 4-benzyloxycarbonylmethyl-2-((N-benzyloxycarbonyl-(L)-phenylalanyl)amino)thiazole
NMR (in CDCl₃) δ: 3.03~3.38 (m, 2H), 3.69 (s, 2H), 4.73~4.89 (m, 1H), 5.07~5.09 (m, 2H), 5.14 (s, 2H), 5.55~5.70 (m, 1H), 6.78 (s, 1H), 7.04~7.41 (s, 1H).

(2) The compounds obtained in the above (1) and the corresponding starting compounds were treated in the same manner as in Example 48-(2), respectively, to obtain the following compounds.

49-(2): 4-benzyloxycarbonyl-5-{2-[N-((1S)-1-benzyloxycarbonyl-3-(2-thienyl)propyl)-(L)-phenylalanyl]aminoethyl}oxazole
State: syrup
NMR (in CDCl₃) δ: 1.66 (br s, 1H), 1.5~1.9 (m, 2H), 2.31~2.39 (m, 2H), 2.60 (dd, 1H), 3.13~3.33 (m, 5H), 3.33~3.49 (m, 2H), 5.02, 5.11 (ABq, 2H), 5.35 (s, 2H), 6.53 (m, 1H), 6.85 (m, 1H), 7.08 (m, 1H), 7.16~7.52 (m, 16H), 7.69 (s, 1H).

50-(2): 3-benzyloxycarbonyl-1-{[N-((1S)-1-benzyloxycarbonyl-3-phenylpropyl)-(L)-phenylalanyl]amino}benzene
State: syrup
NMR (in CDCl₃) δ: 1.60~2.25 (m, 4H), 2.51~3.02 (m, 2H), 3.13~3.45 (m, 2H), 4.98, 5.08 (ABq, 2H), 5.32, 5.41 (ABq, 2H), 6.85~7.44 (m, 24H), 7.7~8.0 (m, 1H).

51-(2): 4-benzyloxycarbonylmethyl-2-{(N-((1S)-1-benzyloxycarbonyl-3-phenylpropyl)-(L)-phenylalanyl)amino}thiazole
State: syrup
NMR (in CDCl₃) δ: 1.85~2.06 (m, 2H), 2.07~2.29 (m, 2H), 2.53~2.76 (m, 2H), 2.81~3.00 (m, 1H), 3.44~3.56 (m, 1H), 3.76 (s, 2H), 5.15~5.17 (m, 4H), 6.80~7.42 (m, 21H).

EXAMPLES 52 TO 68

The products obtained in Examples 26 to 32, 36 to 39, 41 to 43, 46, 47 and 49 were treated in the same manner as in Examples 15, respectively, to obtain compounds shown in the following Tables 16 to 18.

TABLE 16

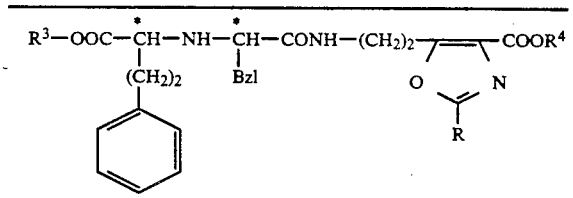

| Example No. | R | $R^3$ | $R^4$ | Physical properties |
|---|---|---|---|---|
| 52 | —CH₃ | H | H | M.P. 174~175° C. (dec.) |

TABLE 16-continued $$R^3-OOC-\overset{*}{C}H-NH-\overset{*}{C}H-CONH-(CH_2)_2-\underset{R}{\underset{O\diagup\diagdown N}{\diagup\diagdown}}-COOR^4$$

with CH(CH₂)₂-phenyl on first CH and Bzl on second CH.

| Example No. | R | R³ | R⁴ | Physical properties |
|---|---|---|---|---|
| 53 | phenyl | " | " | M.P. 207~209° C. (dec.) |
| 54 | H | t-Bu | " | M.P. 128~209° C. |
| 55 | " | H | n-Oct | M.P. 191~192° C. |
| 56 | " | " | n-Bu | M.P. 217~218° C. |
| 57 | " | " | i-Pr | M.P. 212~213° C. |
| 58 | —OH | " | H | M.P. 105° C. (dec.) |

TABLE 17

$$HOOC-\overset{*}{C}H-NH-\overset{*}{C}H-CONH-(CH_2)_m-\underset{Y^1\diagup\diagdown N}{\diagup\diagdown}-COOH$$

with R¹ on first CH and CH₂-R² on second CH.

| Example No. | R¹ | R² | Y¹ | m | Physical properties |
|---|---|---|---|---|---|
| 59 | —CH₂CH₂-phenyl | phenyl | NH | 2 | M.P. 178° C. (dec.) |
| 60 | " | " | O | 3 | M.P. 179~181° C. |
| 61 | " | cyclohexyl (H) | " | 2 | M.P. 125° C. (dec.) |
| 62 | —CH₂CH(CH₃)₂ | phenyl | " | " | M.P. 183~185° C. |
| 63 | —CH₂CH₂-cyclohexyl (H) | " | " | " | M.P. 187° C. (dec.) |
| 64 | —CH₂CH₂-phenyl | thienyl (S) | " | " | M.P. 110~113° C. (dec.) |
| 65 | —CH₂CH₂CH(CH₃)₂ | phenyl | " | " | M.P. 124~127° C. (dec.) |

TABLE 18

$$R^3OOC-\overset{*}{C}H-NH-\overset{*}{C}H-CONH-(CH_2)_2-\underset{Y^1\diagup\diagdown N}{\diagup\diagdown}-COOH$$

with R¹ on first CH and Bzl on second CH.

| Example No. | R¹ | R³ | Y¹ | Physical properties |
|---|---|---|---|---|
| 66 | —(CH₂)₇CH₃ | t-Bu | O | M.P. 136~138° C. |
| 67 | —CH₂-phenyl | —CH₂CH₃ | " | M.P. 53~56° C. |
| 68 | —CH₂CH₂-phenyl | t-Bu | S | M.P. 135~136° C. (dec.) |

EXAMPLE 69

A mixture of 2.6 g of the compound obtained in Example 1, 0.4 ml of methyl iodide, 0.83 g of potassium carbonate and 3 ml of hexamethylphosphoric triamide was stirred at room temperature overnight. Then, ethyl acetate was added to the mixture, and the insolubles were removed by filtration. The filtrate was washed and dried, and then the solvent was removed. The residue was purified by silica gel column chromatography (solvent: chloroform:ethyl acetate=95:5) to obtain 1.81 g (Yield: 68%) of 4-benzyloxycarbonyl-5-(2-[N-((1S)-1-benzyloxycarbonyl-3-phenylpropyl)-N-methyl-(L)-phenylalanyl]aminoethyl}oxazole as an oily product.

NMR (in CDCl₃) δ: 1.65 (s, 1H), 1.65~1.97 (m, 2H), 2.35 (s, 3H), 2.35~2.54 (m, 2H), 2.65~2.82 (m, 1H), 3.00~3.56 (m, 7H), 4.92~5.17 (m, 2H), 5.32 (s, 2H), 6.99~7.43 (m, 20H), 7.65 (s, 1H).

EXAMPLES 70 AND 71

The compounds obtained in Examples 50 and 69 were treated in the same manner as in Example 15 to obtain the following compounds.

70: 3-carboxy-1-{([N-((1S)-1-carboxy-3-phenylpropyl)-(L)-phenylalanyl]amino}benzene
M.P.: 201°~202° C. (decomposed)
71: 4-carboxy-5-(2-(N-((1S)-1-carboxy-3-phenylpropyl)-N-methyl-(L)-phenylalanyl]aminoethyl}oxazole
M.P.: 104°~106° C.

EXAMPLES 72 AND 73

The compounds obtained in Examples 49 and 51 were treated in the same manner as in Example 23 to obtain the following compounds.

72 4-carboxy-5-{2-(N-((1S)-1-carboxy-3-(2-thienyl)-propyl)-(L)-phenylalanyl]aminoethyl}oxazole
M.P.: 125°~127° C. (decomposed)
73: 4-carboxymethyl-2-([N-((1S)-1-carboxy-3-phenylpropyl)-(L)-phenylalanyl]amino}thiazole
M.P.: 178° C. (decomposed)

EXAMPLE 74

0.35 g of the compound obtained in Example 35, 0.88 ml of 2N-NaOH and 20 ml of methanol were stirred overnight at room temperature, and then water was added thereto. Methanol was removed and the residue was extracted with ethyl ether. Then, the aqueous layer was neutralized with 1N-HCl and extracted with ethyl acetate. The extract was washed and dried, and then the solvent was removed. The residue was powdered by adding isopropyl ether to obtain 0.18 g of 4-carboxy-5-{2-[N-((1S)-1-carboxy-2-phenylethyl)-3-(4-methoxyphenyl)-(L)-alanyl]aminoethyl}oxazole.
M.P.: 103°~106° C.

EXAMPLES 75 TO 80

The compounds obtained in Examples 26, 33 to 35 and 46 were treated in the same manner as in Example 74 to obtain compounds shown in the following Table 19.

TABLE 19

$$HOOC-\overset{*}{CH}-N-\overset{*}{CH}-CONH-(CH_2)_m \underset{Y^1 \diagdown N}{\diagup\!\!\!\diagdown} COOH$$
$$\overset{|}{R^1} \quad \overset{|}{R^7} \quad \overset{|}{CH_2}$$
$$\overset{|}{R^2}$$

| Example No. | R¹ | R² | R⁷ | Y¹ | m | Physical properties |
|---|---|---|---|---|---|---|
| 75 | —CH₂—(phenyl) | (phenyl) | H | O | 2 | M.P. = 152~154° C. |
| 76 | —CH₂CH₂—(phenyl) | —(phenyl)—OCH₃ | " | " | " | M.P. = 117~119° C. |
| 77 | —CH₂—(phenyl) | (indolyl, NH) | " | " | " | M.P. = 147° C. (dec.) |
| 78 | " | —(phenyl)—OCH₃ | —CH₃ | " | " | M.P. = 103~106° C. |
| 79 | " | (phenyl) | H | S | " | M.P. = 188~189° C. |
| 80 | —CH₂CH₂—(phenyl) | " | " | O | 1 | M.P. = 175~178° C. |

EXAMPLE 81

(1) A mixture of 1.2 g of 1-tert-butoxycarbonyl-2-phenylethanethiol, 0.22 g of sodium hydride (60% oil) and 20 ml of dimethylformamide was stirred at room temperature for 30 minutes. Then, under ice-cooling, a solution of 1.7 g of benzyl 2-bromo-3-phenylbutyrate dissolved in 5 ml of dimethylformamide was added dropwise to the mixture, and the mixture was stirred at room temperature for 1 hour. Ethyl ether was added to the mixture, and the mixture was washed. The solvent was removed, and the residue was purified by silica gel chromatography (solvent: hexane:ethyl ether=95:5) to obtain 1.25 g (Yield: 51%) of 1-benzyloxycarbonyl-3-phenylpropyl-1-tert-butoxycarbonyl-2-phenylethyl sulfide as an oily product.

NMR (in CDCl$_3$) δ: 1.30 (m, 9H), 1.96~2.24 (m, 2H), 2.59~3.14 (m, 4H), 3.35~3.66 (m, 2H), 5.12 (m, 2H), 7.06~7.36 (m, 15H).

(2) A mixture of 1.47 g of the product obtained, 1.71 g of anisole and 10 ml of trifluoroacetic acid was stirred at room temperature for 1 hour, and then the solvent was removed. Toluene was added to the residue, and the solvent was removed again. Said operation was repeated twice. 0.86 g of the product obtained, 0.55 g of 1-hydroxybenzotriazole.hydrate, 0.69 g of 1-ethyl-3-(3-dimethylaminopropyl)carbodiimide.hydrochloride and 0.5 ml of triethylamine were mixed at −20° C., and then the mixture was stirred overnight while returning the temperature gradually to room temperature. The solvent was removed, and ethyl acetate was added to the residue. The mixture was washed and dried, and then the solvent was removed. The residue was purified by silica gel chromatography (solvent: hexane:ethyl acetate=5:1) to obtain 1.13 g (Yield: 54%) of 4-benzyloxycarbonyl-5-{[3-phenyl-2-((1S)-1-benzyloxycarbonyl-3-phenylpropylthio)propionyl]aminoethyl}oxazole as an oily product.

NMR (in CDCl$_3$) δ: 1.89 (m, 1H), 2.12 (m, 1H), 2.60 (m, 2H), 2.82 (m, 1H), 2.99~3.52 (m, 7H), 5.10 (m, 2H), 5.3 (m, 2H), 6.93~7.41 (m, 20H), 7.65 (s, 1H).

(3) A mixture of 1.00 g of the product obtained, 2 g of palladium black and 50 ml of methanol was stirred under hydrogen atmosphere (3 atm.) overnight. The catalyst was removed by filtration, and then the solvent was removed to obtain 0.69 g (Yield: 95%) of 4-carboxy-5-{[3-phenyl-(2S)-2-((1S)-1-carboxy-3-phenylpropylthio)propionyl]aminoethyl}oxazole as an oily product.

NMR (DMSO-d$_6$) δ: 1.75~1.98 (m, 2H), 2.22~2.39 (m, 1H), 2.50~2.62 (m, 2H), 2.73~2.89 (m, 2H), 3.01~3.36 (m, 5H), 3.36~3.66 (m, 1H), 7.15~7.37 (m, 10H), 8.25, 8.26 (s, s, 1H).

REFERENCE EXAMPLE 1

(1) A mixture of 33.5 g of N-benzyloxycarbonyl-β-alanine, 15 g of methyl isocyanoacetate, 31.8 g of diethylphosphorylcyanide, 23 g of 1,8-diazabicyclo[5.4.0]undec-7-ene, 42 ml of triethylamine and 300 ml of dimethylformamide was stirred at room temperature overnight. Then, the solvent was removed, and ethyl acetate was added to the mixture. The mixture was washed and dried, and then the solvent was removed. The residue was purified by silica gel chromatography and crystallized from isopropyl ether, followed by recrystallization from an ethyl acetate-isopropyl ether mixed solution, to obtain 22.6 g of 4-methoxycarbonyl-5-{2-(benzyloxycarbonylamino)ethyl}oxazole.

M.P.: 68°~70° C.

(2) 5 g of the product obtained and 50 ml of a 25% hydrogen bromide-acetic acid solution were stirred at room temperature for 15 minutes, and then the solvent was removed. The residue was crystallized from ethyl ether to obtain 4-methoxycarbonyl-5-(2-aminoethyl)oxazole monohydrobromide as crude crystals, which was used in the next reaction without purification.

REFERENCE EXAMPLE 2

(1) The corresponding starting compound was treated in the same manner as in Reference example 1-(1) to obtain the following compound.
4-benzyloxycarbonyl-5-(3-tert-butoxycarbonylamino)propyl}oxazole
M.P.: 124°~126° C.

(2) The product obtained above was treated in the same manner as in Reference example 1-(2) to obtain 4-benzyloxycarbonyl-5-(3-Aminopropyl)oxazole.monohydrobromide.

REFERENCE EXAMPLES 3 TO 9

(1) The corresponding starting compounds were treated in the same manner as in Reference example 1-(1) to obtain compounds shown in the following Table 20.

TABLE 20

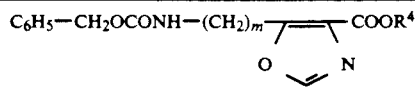

| Reference example No. | R$^4$ | m | Physical properties |
| --- | --- | --- | --- |
| 3-(1) | Bzl | 1 | M.P. 124~126° C. |
| 4-(1) | Bzl | 2 | M.P. 76~79° C. |
| 5-(1) | t-Bu | " | Oily product |
| 6-(1) | n-Oct | " | M.P. 44~46° C. |
| 7-(1) | n-Bu | " | M.P. 43~44° C. |
| 8-(1) | i-Bu | " | Oily product |
| 9-(1) | i-Pr | " | Oily product |

(2) The products obtained above were treated in the same manner as in Reference example 1-(2) to obtain compounds shown in the following Table 20-a.

TABLE 20-a

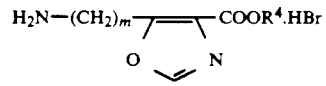

| Reference example No. | R$^4$ | m |
| --- | --- | --- |
| 3-(2) | Bzl | 1 |
| 4-(2) | Bzl | 2 |
| 5-(2) | t-Bu | 2 |
| 6-(2) | n-Oct | 2 |
| 7-(2) | n-Bu | 2 |
| 8-(2) | i-Bu | 2 |
| 9-(2) | i-Pr | 2 |

REFERENCE EXAMPLE 10

(1) A mixture of 30 g of 4-methoxycarbonyl-5-{2-benzyloxycarbonylamino)ethyl}oxazole, 75 ml of a 2N sodium hydroxide aqueous solution and 75 ml of methanol was stirred at room temperature for 3 hours. Methanol was removed, and then 1N hydrochloric acid was added dropwise to the residue under ice cooling. The crystals obtained were collected by filtration to obtain 25.8 g of 4-carboxy-5-{2-(benzyloxycarbonylamino)ethyl}oxazole, which was used in the next reaction without purification.

(2) A mixture of 2.9 g of the product obtained, 1.81 g of dicyclohexylamine, 2.33 g of ethyl iodide and 20 ml of dimethylformamide was stirred at room temperature overnight. The solvent was removed, and then 30 ml of ethyl acetate was added to the residue. The mixture was washed and died, and then the solvent was removed. The residue was purified by silica gel chromatography and crystallized from isopropyl ether, followed by recrystallization from an ethyl acetate-n-hexane mixed solution, to obtain 2.89 g of 4-ethoxycarbonyl-5-{2-(benzyloxycarbonylamino)ethyl}oxazole.

M.P : 46°~48° C.

(3) 3.18 g of the product obtained was treated in the same manner as in Reference example 1-(2) to obtain 4-ethoxycarbonyl-5-(2-aminoethyl)oxazole.monohydrobromide as crude crystals, which was used in the next reaction without purification.

REFERENCE EXAMPLE 11

(1) A mixture of 36.5 g of 4-methoxycarbonyl-5-{2-(benzyloxycarbonylamino)ethyl}oxazole, 90 ml of concentrated hydrochloric acid and 270 ml of methanol was stirred at 55° C. for 6 hours. After removing the solvent, the residue was dissolved in tetrahydrofuran, and the solution was neutralized with 21 ml of triethylamine. Further, the solution was cooled to 0° C., and to the solution was added 450 ml of formic acid and was added dropwise 150 ml of acetic anhydride at the same temperature. The mixture was stirred at 10° C. for 3 hours, and ice water was added thereto. The solvent was removed, and then the residue was dissolved in ethyl acetate. The mixture was washed and dried, and then the solvent was removed. The residue was purified by silica gel chromatography to obtain 20 g of methyl 3-oxo-5-(benzyloxycarbonylamino)-2-(formylamino)-pentanoate as a colorless oily product.

NMR (CDCl$_3$) δ: 2.86~3.13 (m, 2H), 3.45~3.53 (m, 2H), 3.79 (s, 3H), 5.09 (s, 2H), 5.29 (d, 1H), 5.1~5.5 (br, 1H), 6.8~7.0 (m, 1H), 7.34 (s, 5H), 8.22 (s, 1H).

(2) A mixture of 20 g of the product obtained, 12.5 g of 2,4-bis(4-methoxyphenyl)-1,3-dithia-2,4-diphosphetane-2,4-disulfide and 300 ml of toluene was refluxed for 30 minutes. After removing the solvent, the residue was purified by silica gel chromatography and crystallized from isopropyl ether, followed by recrystallization from an ethyl acetate-isopropyl ether mixed solution to obtain 10.5 g of 4-methoxycarbonyl-5-{2-(benzyloxycarbonylamino)ethyl}thiazole.

M.P.: 108°~110° C.

(3) The product obtained was treated in the same manner as in Reference example 10-(1) to obtain 4-carboxy-5-{2-(benzyloxycarbonylamino)ethyl}thiazole as crude crystals, which was used in the next reaction without purification.

REFERENCE EXAMPLES 12 TO 16

(1) The corresponding compounds were treated in the same manner as in Reference example 11-(1) and (2) to obtain compounds shown in the following Table 21.

TABLE 21

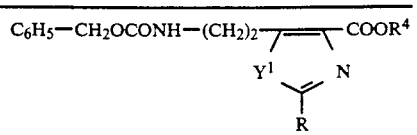

| Reference example No. | Y$^1$ | R$^4$ | R | Physical properties |
|---|---|---|---|---|
| 12-(1) | S | C$_2$H$_5$ | H | M.P. 89~91° C. |
| 13-(1) | S | Bzl | H | M.P. 99~100° C. |
| 14-(1) | O | Bzl | CH$_3$ | M.P. 88~89° C. |
| 15-(1) | O | Bzl | C$_6$H$_5$ | M.P. 83~84° C. |
| 16-(1) | O | Bzl | OH | M.P. 111~113° C. |

(2) The corresponding compounds were treated in the same manner as in Reference example 1-(2) to obtain compounds shown in the following Table 22.

TABLE 22

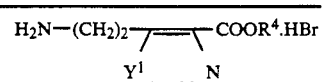

| Reference example No. | Y$^1$ | R$^4$ |
|---|---|---|
| 12-(2) | S | C$_2$H$_5$ |
| 13-(2) | S | Bzl |
| 14-(2) | O | Bzl |
| 15-(2) | O | Bzl |
| 16-(2) | O | Bzl |

REFERENCE EXAMPLE 17

(1) The corresponding compounds were treated in the same manner as in Reference example 11-(1) and (2) to obtain 1-tert-butoxy-5-benzyloxycarbonyl-4-{2-tert-butoxycarbonylamino)ethyl}imidazole.

M.P.: 124°~126° C.

(2) The product obtained above was treated in the same manner as in Reference example 1-(2) to obtain 5-benzylcarbonyl-4-(2-aminoethyl)imidazole.monohydrobromide.

REFERENCE EXAMPLE 18

(1) To a mixture of 2.9 g of 4-carboxy-5-{2-(benzyloxycarbonylamino)ethyl}oxazole, 4.9 g of pyridine, 6 ml of tert-butyl alcohol and 50 ml of chloroform was added dropwise 1.84 g of phosphoryl chloride at −10° C., and the mixture was stirred at the same temperature for 1 hour and further at room temperature overnight. The mixture was washed and dried, and then the solvent was removed. The residue was purified by silica gel chromatography to obtain 2.85 g of 4-tert-butoxycarbonyl-5-{2-(benzyloxycarbonylamino)ethyl}oxazole as a colorless oily product.

NMR (CDCl$_3$) δ: 1.58 (s, 9H), 3.22~3.28 (m, 2H), 3.50~3.59 (m, 2H), 5.08 (s, 2H), 7.33 (s, 5H), 7.74 (s, 1H).

(2) 3.45 g of the product obtained and 0.9 g of oxalic acid were treated in the same manner as in Reference example 1-(2). The crystals obtained were recrystallized from a tetrahydrofuran-isopropyl ether mixed solution to obtain 2.8 g of 4-tert-butoxycarbonyl-5-(2-aminoethyl)oxazole.monooxalate.

M.P.: 116°~120° C.

The dicarboxylic acid derivative (I) which is the desired compound of the present invention, an ester thereof and a pharmaceutically acceptable salt thereof have excellent neutral metalloendopeptidase inhibiting activity, and exhibit excellent diuretic and vasodilating activities, and inhibiting activity on renin and aldosterone secretion based on the inhibiting effect of atrial natriuretic peptide (ANP) degradation. Moreover, the compounds of the present invention are low in toxicity and have high safety as a medicine. Thus, they can be used as a curing and/or prophylactic medicine for patients with hypertension, heart failure and renal insufficiency. Particularly for curing hypertension, angiotensin-converting enzyme inhibiting agents (ACE inhibiting agents) such as captopril and derapril hydrochloride have been clinically used at present. However, the desired product of the present invention, an ester thereof and pharmaceutically acceptable salts thereof have excellent characteristics in that they have effects also on low renin hypertension while the ACE inhibiting agents have relatively small effects thereon.

For example, when hypotensive activity is examined by using hypertension rats, in each group of rats orally administered with 30 mg/kg of 4-ethoxycarbonyl-5-{2-[N-((1S)-1-ethoxycarbonyl-3-phenylpropyl)-(L)-phenylalanyl]aminoethyl}thiazole, 4-carboxy-5-{2-[N-((1S)-1-ethoxycarbonyl-3-phenylpropyl)-(L)-phenylalanyl]aminoethyl}thiazole, 4-ethoxycarbonyl-5-{2-[N-((1S)-1-carboxy-3-phenylpropyl)-(L)-phenylalanyl]aminoethyl}thiazole or 4-carboxy-5-{2-[N-((1S)-1-ethoxycarbonyl-3-phenylpropyl)-(L)-phenylalanyl]aminoethyl}oxazole which is the desired compound of the present invention, significant hypotensive activity was observed as compared with that of the control group of rats to which purified water was orally administered.

Some known ANP degradation inhibitors have not only neutral metalloendopeptidase inhibiting activity but also angiotensin-converting enzyme inhibiting activity. However, the desired compound of the present invention have both characteristics of being weak in angiotensin-converting enzyme inhibiting activity and having neutral metalloendopeptidase inhibiting activity more selectively.

We claim:

1. A N,3-substituted alaninamide compound represented by the formula (I):

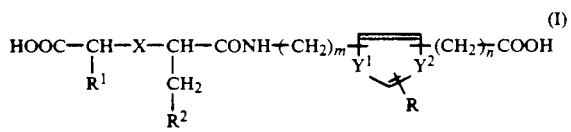

wherein R represents hydrogen, lower alkyl, phenyl or hydroxy; $R^1$ represents straight or branched alkyl of 1 to 10 carbons or lower alkyl substituted by aryl, thienyl or cycloalkyl of 4 to 8 carbons; $R^2$ represents aryl, lower alkoxy substituted aryl, cycloalkyl of 4 to 8 carbons, thienyl or indolyl; X represents sulfur, oxygen, imino or lower substituted imino; $Y^1$ represents imino, oxygen or sulfur and $Y^2$ represents nitrogen, or $Y^1$ represents vinylene and $Y^2$ represents: —CH=; m represents 0 to 3; and n represents 0 or 1, and wherein the carboxyl groups are free or one or two carboxyl groups are esterified or pharmaceutically acceptable salts thereof.

2. The compound according to claim 1, wherein $R^1$ is straight or branched alkyl of 1 to 10 carbons or lower alkyl substituted by phenyl, thienyl or cyclohexyl; $R^2$ is phenyl, lower alkoxy substituted phenyl, cyclohexyl, thienyl or indolyl; and X is sulfur, oxygen, imino or lower alkyl substituted imino.

3. The compound according to claim 2, wherein X is sulfur, imino or lower alkyl substituted imino.

4. The compound according to claim 3, wherein $R^1$ is straight or branched alkyl of 1 to 10 or lower alkyl substituted by phenyl or thienyl; $R^2$ is phenyl, lower alkoxy substituted phenyl or indolyl; X is imino or lower alkyl substituted imino; $Y^1$ is imino, oxygen or sulfur; $Y^2$ is nitrogen; m is 2 and n is 0.

5. The compound according to claim 4, wherein R is hydrogen; $R^1$ is straight or branched alkyl of 1 to 10 carbons or phenyl substituted lower alkyl; $R^2$ is phenyl or indolyl; X is imino; $Y^1$ is oxygen or sulfur; and $Y^2$ is nitrogen.

6. The compound according to claim 3, wherein R is hydrogen, methyl, phenyl or hydroxyl; $R^1$ is sec-butyl, sec-pentyl, n-octyl, benzyl, phenylethyl, thienylethyl or cyclohexylethyl; $R^2$ is phenyl, methoxyphenyl, cyclohexyl, thienyl or indolyl; and X is sulfur, imino or methylimino.

7. The compound according to claim 4, wherein R is hydrogen, methyl or phenyl; $R^1$ is n-octyl, phenylethyl or thienylethyl; $R^2$ is phenyl, methoxyphenyl or indolyl; and X is imino or methylimino.

8. The compound according to claim 7, wherein R is hydrogen; $R^1$ is n-octyl or phenylethyl; $R^2$ is phenyl or indolyl; X is imino; $Y^1$ is oxygen or sulfur; and $Y^2$ is nitrogen.

9. The compound according to claim 1, wherein one or two carboxyl groups are esterified by straight or branched alkyl of 1 to 10 carbons or phenyl lower alkyl.

10. The compound according to claim 1, wherein both of two asymmetric carbon atoms have S configurations.

11. A pharmaceutical composition which comprises an effective amount of a N,3-disubstituted alaninamide derivative of the formula (I) as set forth in claim 1 in admixture of a conventional pharmaceutically acceptable carrier or diluent therefor.

12. Method for treatment of hypertension, heart failure and/or renal insufficiency in a warm-blooded animal which comprises administering an effective amount of a N,3-disubstituted alaninamide derivative of the formula (I) as set forth in claim 1 to said warm-blooded animal suffering from the disease.

* * * * *